US011896695B2

(12) United States Patent
Hicks et al.

(10) Patent No.: US 11,896,695 B2
(45) Date of Patent: Feb. 13, 2024

(54) COSMETIC COMPOSITIONS

(71) Applicant: THE BOOTS COMPANY PLC, Nottingham (GB)

(72) Inventors: Jake Thomas Hicks, Nottingham (GB); Marco Demurtas, Valbrembo (IT); Christopher John Elms, Nottingham (GB); Paul James Tomlinson, Derby (GB); Michael David Bell, Alfreton (GB)

(73) Assignee: THE BOOTS COMPANY PLC, Nottingham (GB)

( * ) Notice: Subject to any disclaimer, the term of this patent is extended or adjusted under 35 U.S.C. 154(b) by 527 days.

(21) Appl. No.: 17/268,225

(22) PCT Filed: Aug. 5, 2019

(86) PCT No.: PCT/EP2019/025254
§ 371 (c)(1),
(2) Date: Feb. 12, 2021

(87) PCT Pub. No.: WO2020/035168
PCT Pub. Date: Feb. 20, 2020

(65) Prior Publication Data
US 2021/0161781 A1    Jun. 3, 2021

(30) Foreign Application Priority Data
Aug. 15, 2018  (EP) .................................... 18020390

(51) Int. Cl.
*A61K 8/365* (2006.01)
*A61K 8/06* (2006.01)
*A61K 8/36* (2006.01)
*A61K 8/73* (2006.01)
*A61K 8/86* (2006.01)
(Continued)

(52) U.S. Cl.
CPC .............. *A61K 8/365* (2013.01); *A61K 8/062* (2013.01); *A61K 8/361* (2013.01); *A61K 8/73* (2013.01); *A61K 8/86* (2013.01); *A61K 8/88* (2013.01); *A61Q 19/10* (2013.01)

(58) Field of Classification Search
CPC ........ A61K 8/365; A61K 8/062; A61K 8/361; A61K 8/73; A61K 8/86; A61K 8/88; A61Q 19/10
See application file for complete search history.

(56) References Cited

U.S. PATENT DOCUMENTS 2,798,053 A    7/1957  Brown
5,373,044 A    12/1994 Adams et al.
(Continued)

FOREIGN PATENT DOCUMENTS

CN   102548532 A   7/2012
CN   103987372 A   8/2014
(Continued)

OTHER PUBLICATIONS

International Application No. PCT/EP2019/025254, International Search Report and Written Opinion, dated Oct. 2, 2019.
(Continued)

*Primary Examiner* — Deborah D Carr
(74) *Attorney, Agent, or Firm* — MARSHALL, GERSTEIN & BORUN LLP

(57) ABSTRACT

According to the present invention there is provided composition in the form of an oil-in-water emulsion having a viscosity of between 15,000 cP (15 Pa-s) and 45,000 cP (45 Pa-s) at 23° C., having a pH of between 2 and 6 and comprising: (i) at least 1.6 wt. % of at least one cross-linked anionic polyelectrolyte resulting from the polymerisation of partially or completely salified 2-methyl 2-[(1-oxo 2-propenyl)amino]1-propane sulfonic acid, with at least one neutral monomer chosen from the N,N-dialkyl acrylamides, wherein each of the alkyl groups comprises between one and four carbon atoms, and at least one monomer of formula (B): wherein R represents a linear or branched alkyl radical comprising eight to twenty carbon atoms and n represents a number greater than or equal to one and less than or equal to twenty, in the presence of at least one cross-linking agent; (ii) at least 4 wt. % of at least one polysorbate; (iii) at least 0.1 wt. % of at least one polysaccharide gum; and (iv) between 6 wt. % and 30 wt. % water. The present invention also provides a composition as defined above obtainable by a process comprising the following steps: (a) in one vessel, homogenising the polysaccharide gum (iii) into the aqueous phase comprising the water at a temperature of between 60° C. and 90° C.; (b) in a vessel separate from that in (a), homogenising the cross-linked anionic polyelectrolyte (i) and the polysorbate (ii) into the oil phase at a temperature of between 60° C. and 90° C.; and (c) combining the ingredients of (a) with the ingredients of (b) through homogenisation at a temperature of between 60° C. and 90° C.

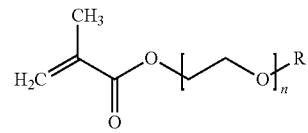

(B)

19 Claims, No Drawings

(51) Int. Cl.
  *A61K 8/88* (2006.01)
  *A61Q 19/10* (2006.01)

(56) References Cited

U.S. PATENT DOCUMENTS

| | | |
|---|---|---|
| 10,035,143 B2 | 7/2018 | Braun et al. |
| 2012/0172457 A1 | 7/2012 | Braun et al. |
| 2014/0350125 A1 | 11/2014 | Merat |
| 2015/0335567 A1 | 11/2015 | Merat |
| 2016/0167040 A1* | 6/2016 | Braun .................. A61K 8/8158 521/38 |

FOREIGN PATENT DOCUMENTS

| | | |
|---|---|---|
| CN | 104902961 A | 9/2015 |
| CN | 105392811 A | 3/2016 |
| EP | 0301532 A2 | 2/1989 |
| EP | 0816403 A2 | 1/1998 |
| EP | 1069142 A1 | 1/2001 |
| EP | 1116733 A1 | 7/2001 |
| FR | 2910899 A1 | 7/2008 |
| FR | 2940111 A1 | 6/2010 |
| WO | WO-2008087326 A2 | 7/2008 |
| WO | WO-2011/030044 A1 | 3/2011 |

OTHER PUBLICATIONS

Office Action (and English translation) from Chinese Application No. 201980053112.4 dated Nov. 28, 2022.

* cited by examiner

COSMETIC COMPOSITIONS

FIELD OF INVENTION

The present invention relates to novel, non-stringy, oil-in-water emulsion, paste formulations comprising a polyelectrolyte, a polysorbate, a polysaccharide gum and between 6 wt. % and 30 wt. % water.

BACKGROUND TO THE INVENTION

Cosmetic compositions presented in the form of oil-in-water emulsions marketed by the cosmetics industry very frequently comprise synthetic thickening polymers for increasing the viscosity of said oil-in-water emulsions which may be presented in the form of creams, lotions and which are applied directly to the skin.

These synthetic thickening polymers make it possible to thicken the aqueous phases present in said oil-in-water emulsions, thus obtaining either the desired consistency or a stabilisation effect of said emulsion.

The synthetic thickening polymers currently used in these fields are presented in two physical forms, powder form and liquid form for which the polymer is prepared by inverse emulsion radical polymerisation using surfactants, and commonly referred to as inverse latex.

Among the best known synthetic thickening polymers presented in powder form, mention can be made of polymers based on acrylic acid or copolymers based on acrylic acid and the esters thereof Mention may be made for example of the polymers marketed under the brand name CARBOPOL™ and PEMULEN™. They are described in particular in the patents U.S. Pat. Nos. 5,373,044, 2,798,053 and EP0301532.

In cosmetics, homopolymers or copolymers based on 2-acrylamido-2-methyl-propane sulfonic acid and/or salts thereof are also used, again in powder form. These thickening polymers are marketed under the brand name Aristoflex™ and described in particular in the European patents EP0816403, EP1116733 and EP1069142. These synthetic thickeners in powder form are obtained by precipitation polymerisation; the monomer(s) is (or are) placed in solution in an organic solvent such as benzene, ethyl acetate, cyclohexane, tertio-butanol; this method therefore requires numerous successive steps for purifying the end product, to remove any trace of residual solvent.

The cosmetics industry also very widely use thickeners presented in the form of inverse latexes. Mention may be made for example of the thickeners Sepigel™ 305, Simulgel™ 600, Simulgel™ EG, Simulgel™ EPG, Simulgel™ NS, Simulgel™ A, Sepiplus™ 400, Sepiplus™ 250 and Sepiplus™ 265. These thickeners are obtained by inverse emulsion radical polymerisation. They have the advantage of being easier to handle, in particular at ambient temperature, and disperse very quickly in water. Furthermore, these products develop remarkably high thickening performances; these performances are probably the consequence of the method used for the preparation thereof, a dispersed phase radical polymerisation reaction, which results in polymers with very high molecular weights.

Synthetic thickening systems such as those described in FR290899 discloses a linear, branched or cross-linked terpolymer of at least one monomer having a free, partially salified or completely salified strong acid function, with at least one neutral monomer, and at least one monomer of formula (A):

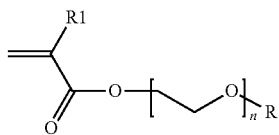

(A)

wherein R1 represents a hydrogen atom or a methyl radical, R represents a linear or branched alkyl radical comprising from eight to thirty carbon atoms and n represents a number greater than or equal to one and less than or equal to fifty. These polymers have very marked thickening properties, in particular in the presence of electrolytes. They function over a wide pH range and make it possible to produce transparent gels. However, formulations with a low pH thickened by some of them do not have satisfactory resistance to salts over the long term and some of them, which contain fatty alcohols, have an unappealing elastic appearance and give sticky sensations to the touch and/or an appearance of a granular and non-continuous cream or emulsion.

It has been shown that these drawbacks could be avoided by selecting some of these terpolymers, which had not been disclosed in the FR2910899, and has developed branched or cross-linked anionic polyelectrolytes, such as those described in WO2011030044, which result from the radical polymerisation of at least one monomer having a partially salified or completely salified strong acid function, with at least one neutral monomer, and at least one monomer of formula (B):

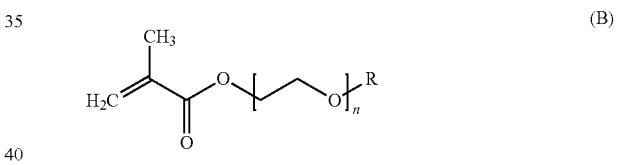

(B)

wherein R represents a linear or branched alkyl radical comprising eight to twenty carbon atoms and n represents a number greater than or equal to one and less than or equal to thirty.

However, when oil-in-water emulsions are prepared using such synthetic thickening terpolymers, a stringy sensory property is observed upon handling. It is therefore necessary to develop novel oil-in-water emulsions, that do not present such stringiness, but which retain a high viscosity in the presence of electrolyte-enriched media and at a low pH.

Polysaccharides have been used for many years as agents for modifying texture and/or rheology for preparing food, cosmetic or pharmaceutical compositions. Depending on the chemical constitution thereof, they may be used as gelling agents and/or as thickening agents. Thickening agent means a chemical compound that increases the viscosity of the medium wherein it is introduced. Gelling agent means a compound that transforms a liquid medium into a structured state, which does not flow, by forming a three-dimensional lattice in the liquid; the gel being considered to be an intermediate state between the liquid state and the solid state.

Polysaccharides are polymers of saccharides. The IUPAC definition of saccharides designates sugars, compounds of sugars strictly speaking and derivatives thereof obtained either by reduction of a carbonyl group, or by oxidation of one or more hydroxyl functions, or by replacing one or more hydroxyl functions with a hydrogen atom, an amine group, a phosphate function or a sulphate function.

The polysaccharides most commonly used for preparing food, cosmetic or pharmaceutical compositions mainly consist of sugars, such as glucose, galactose or mannose or sugar derivatives for which the hydroxyl function of the terminal carbon has been oxidised into a carboxyl function. Two distinct groups can be distinguished among polysaccharides: polysaccharides consisting solely of monosaccharides (or poly-sugars) and polysaccharides consisting of sugar derivatives.

Xanthan gum has for the past few decades become the microbial polyoside most used in industry. Xanthan is a polysaccharide synthesised by bacteria of the genus Xanthomonas and, commercially, only the species X. campestris is used. The main chain of xanthan gum is identical to that of cellulose, that is to say it is formed by β-D-glucose units connected by carbon atoms 1 and 4. There is a branched triholoside every two glucose units in the main chain, in a regular alternating fashion; each branching consisting of a triholoside composed of two mannoses and a glucuronic acid, of the type: β-D-Manp-(1→4)-β-D-GlcAp-(1→2)-α-D-Manp-(1→3) (I. Capron et al., "About the native and renaturated conformation of xanthan exopolysaccharide". 1997). Xanthan gum is available in the form of a sodium, potassium or calcium salt.

FR2940111 describes the use of compositions comprising polysaccharides, which may be associated with hydrophilic gelling agents in particular chosen from among copolymers comprising 2-acrylamido-2-methylpropane sulfonic acid and acrylamide as constituent monomers, or copolymers comprising 2-acrylamido-2-methylpropane sulfonic acid and polyoxyethylenated alkyl methacrylates. These compositions are intended for uses in make-up, having the property of not transferring onto the substrates whereon they are placed in contact as well as the property consisting of resisting water after application on the skin. However, the hydrophilic gelling agents described in the FR2940111 are known not to make it possible to reach high levels of viscosity in the presence of media enriched with electrolytes.

US20140350125 relates to an oil-in-water emulsion comprising an oil phase consisting of at least one oil and/or wax, a cross-linked anionic polyelectrolyte, xanthan gum, acacia gum and a cosmetically acceptable aqueous phase.

US20160167040 relate to novel branched or crosslinked anionic polyelectrolytes and uses thereof as a thickener.

The inventors have therefore sought to develop novel oil-in-water emulsions free from emulsifying surfactants in the stabilising system thereof, retaining a high viscosity and a non-stringy sensory property.

SUMMARY OF THE INVENTION

According to the first aspect, the present invention provides a composition in the form of an oil-in-water emulsion having a viscosity of between 15,000 cP (equivalent to 15 Pascal seconds (Pa·s)) and 45,000 cP (45 Pa·s) at 23° C., having a pH of between 2 and 6 and comprising (i) at least 1.6 wt. % of at least one cross-linked anionic polyelectrolyte resulting from the polymerisation of partially or completely salified 2-methyl 2-[(1-oxo 2-propenyl)amino] 1-propane sulfonic acid, with at least one neutral monomer chosen from the N,N-dialkyl acrylamides, wherein each of the alkyl groups comprises between one and four carbon atoms, and at least one monomer of formula (B):

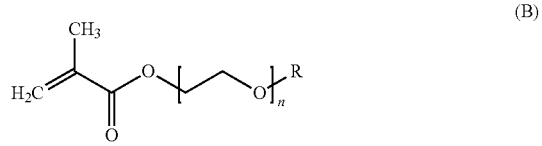

wherein R represents a linear or branched alkyl radical comprising eight to twenty carbon atoms and n represents a number greater than or equal to one and less than or equal to twenty, in the presence of at least one cross-linking agent; (ii) at least 4 wt. % of at least one polysorbate; (iii) at least 0.1 wt. % of at least one polysaccharide gum; and (iv) between 6 wt. % and 30 wt. % water.

In one embodiment, the composition has a pH of between 3 and 5, preferably between 3.4 and 4.5.

In one embodiment, the at least one polysorbate is present at a concentration of between 4 wt. % and 20 wt. %, preferably between 4 wt. % and 15 wt. %, more preferably between 5 wt. % and 12 wt. %, more preferably between 6 wt. % and 10 wt. %. In one embodiment, the fatty acid associated with the polyoxyethylene sorbitan part of the polysorbate comprises between sixteen and eighteen carbon atoms, preferably wherein the fatty acid is saturated, more preferably wherein the fatty acid comprises eighteen carbon atoms and is saturated.

In one embodiment, the at least one polysaccharide gum is present at a concentration of between 0.01 wt. % and 1 wt. %, preferably between 0.1 wt. % and 0.5 wt. %, more preferably between 0.2 wt. % and 0.3 wt. %. In one embodiment, the polysaccharide gum is uncharged. Preferably the polysaccharide gum is xanthan gum.

In one embodiment, the water is present at a concentration of between 10 wt. % and 28 wt. %, preferably between 15 wt. % and 25 wt. %, more preferably between 18 wt. % and 24 wt. %, more preferably between 19 wt. % and 23 wt. %.

In one embodiment, the neutral monomer of the at least one cross-linked anionic polyelectrolyte is N,N-dimethyl acrylamide, acrylamide or (2-hydroxy-ethyl) acrylate. In one embodiment, R of formula (B) represents an alkyl radical having between 12 and 18 carbon atoms. In one embodiment, the at least one polyelectrolyte is present at a concentration of between 1.6 wt. % and 4 wt. %, preferably between 1.7 wt. % and 3 wt. %, more preferably between 1.8 wt. % and 2.5 wt. %.

In one embodiment, the composition has a viscosity of between 17,000 cP (17 Pa·s) and 45,000 cP (45 Pa·s), preferably between 20,000 cP (20 Pa·s) and 40,000 cP (40 Pa·s), at 23° C.

In one embodiment, the composition further comprises a mild acid suitable for exfoliating the skin. In a preferred embodiment, the mild acid is selected from the list comprising glycolic acid, lactic acid, citric acid, malic acid, tartaric acid and combinations thereof, preferably glycolic acid.

According to a further aspect, the present invention provides a composition as defined above obtainable by a process comprising the following steps: (a) in one vessel, homogenising the polysaccharide gum (iii) into the aqueous phase comprising the water at a temperature of between 60° C. and 90° C.; (b) in a vessel separate from that in (a), homogenising the cross-linked anionic polyelectrolyte (i) and the polysorbate (ii) into the oil phase at a temperature of between 60° C. and 90° C.; and (c) combining the ingredients of (a) with the ingredients of (b) through homogenisation at a temperature of between 60° C. and 90° C.

DETAILED DESCRIPTION OF THE INVENTION

In the present application, the term "about" or "approximately" or "around" may encompass ±10%, such as ±5%, for example ±2%, preferably ±1%.

Unless otherwise stated, concentrations of components within the compositions of the present invention are presented as a weight (wt.) percentage (%).

"Oils" means in the present application the compounds and/or mixtures of compounds insoluble in water, being in a liquid aspect at a temperature of 25° C. Among the oils that can be used in the oil phase of the composition that is the subject matter of this invention, the following can be mentioned:

plant oils, such as jojoba oil, phytosqualane, sweet almond oil, copra oil, castor oil, olive oil, rapeseed oil, peanut oil, sunflower oil, wheat germ oil, maize germ oil, soya bean oil, cotton oil, alfalfa oil, poppy oil, pumpkin seed oil, evening primrose oil, millet oil, barley oil, rye oil, safflower oil, candlenut oil, passionflower oil, hazelnut oil, palm oil, shea butter, apricot kernel oil, calophyllum oil, sisymbrium oil, avocado oil, calendula oil, oils derived from flowers or vegetables (preferably jojoba oil);

mineral oils such as paraffin oil, liquid petrolatum, isoparaffins or white mineral oils;

oils of animal origin, such as squalene or squalane;

ethoxylated plant oils;

synthetic oils such as fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate, isocetyl lanolate, monoglycerides, diglycerides and triglycerides of fatty acids such as glycerol triheptanoate, alkybenzoates, hydrogenated oils, poly (alpha-olefins), polyolefins such as polyisobutene, synthetic isoalkanes, such as isohexadecane, isododecane, perfluorinated oils; and silicone oils such as dimethylpolysiloxanes, methylphenyl-polysiloxanes, silicones modified by amines, silicones modified by fatty acids, silicones modified by alcohols, silicones modified by alcohols and fatty acids, silicones modified by polyether groups, modified epoxy silicones, silicones modified by fluorinated groups, cyclic silicones and silicones modified by alkyl groups.

Among the fats that can be associated with the oil phase of the composition that is the subject matter of this invention, saturated or unsaturated fatty alcohols, linear or branched, or saturated or unsaturated fatty acids, linear or branched, can be cited.

In the composition that is the subject matter of this invention, xanthan gum means a heteropolymer of D-glucose, D-mannose, D-glucuronic acid, acetyl and pyruvic acid, obtained by the aerobic fermentation of bacteria of *X. campestris*. Its structure consists of a main chain of β-D-glucose units interconnected by the carbon atoms 1 and 4. A branched triholoside is counted every two glucose units in the main chain, in a regular alternating fashion; each branch consisting of a triholoside composed of two mannoses and a glucuronic acid, of the type: β-D-Manp-(1→4)-β-D-GlcAp-(1→2)-α-D-Manp-(1→3).

"Polysaccharide gum" in the context of the present invention means a polysaccharide capable of causing a large increase in a solution's viscosity, even at small concentrations. In one embodiment, the polysaccharide gum is uncharged (i.e. not a polyelectrolyte). In one embodiment, the polysaccharide gum is xanthan gum.

Xanthan gums are available in the form of a sodium, potassium or calcium salt, and are characterised by a molecular weight of between 1,000,000 and 50,000,000. Xanthan gums are represented for example by the product sold under the trade name Keltrol™ CG-T by the company CP-KELCO and under the trade name Rhodicare™ by the company Rhodia Chemie.

Polysorbates are a class of emulsifiers used in cosmetics to, for example, solubilise essential oils into water-based products. Polysorbates are derived from ethyoxylated sorbitan (a derivative of sorbitol) esterified with monolauric acid (polysorbate 20), monopalmitic acid (polysorbate 40), monostearic acid (polysorbate 60) or monooleic acid (polysorbate 80). In one embodiment, the fatty acid associated with the polyoxyethylene sorbitan part of the polysorbate comprises sixteen and eighteen carbon atoms, thus including polysorbate 40 (palmitic acid comprises sixteen carbon atoms), polysorbate 60 (stearic acid comprises eighteen carbon atoms) and polysorbate 80 (oleic acid comprises eighteen carbon atoms). In one embodiment, the fatty acid associated with the polyoxyethylene sorbitan part of the polysorbate is saturated, thus including polysorbate 20, 40 and 60 (lauric acid, palmitic acid and stearic acid are all saturated). In one embodiment, the fatty acid associated with the polyoxyethylene sorbitan part of the polysorbate is saturated and comprises eighteen carbon atoms, thus including polysorbate 60.

Cross-linked anionic polyelectrolyte means, in the definition of the composition that is the subject matter of this invention, a non-linear cross-linked anionic polyelectrolyte, presented in the state of a three-dimensional lattice insoluble in water, but swellable in water and leading to the obtaining of a chemical gel.

Partially salified or completely salified means in the definition of the cross-linked anionic polyelectrolyte present in the composition as defined above, that said 2-methyl 2-[(1-oxo 2-propenyl)amino] 1-propane sulfonic acid is partially or completely salified, generally in the form of alkaline metal salt, such as for example sodium salt or potassium salt, or in the form of ammonium salt.

Said cross-linked anionic polyelectrolyte used in the composition, as defined above comprises generally between 5% molar and 95% of the monomer from 2-methyl 2-[(1-oxo 2-propenyl)amino] 1-propane sulfonic acid, more particularly between 10% molar and 90% molar, more particularly between 20% molar and 80% molar, and even more particularly between 60% molar and 80% molar.

Said cross-linked anionic polyelectrolyte used in the composition as defined above comprises generally between 4.9% molar and 90% molar of neutral monomer chosen from the N,N-dialkyl acrylamides, wherein each of the alkyl groups comprise between one and four carbon atoms, more particularly between 9.5% molar and 85% molar, more particularly between 15% and 75% molar, and even more particularly between 15% molar and 39.5% molar.

Said cross-linked anionic polyelectrolyte used in the composition as defined above comprises generally between 0.1% molar and 10% molar of monomers of formula (B) and more particularly between 0.5% molar and 5% molar.

In the definition of said cross-linked anionic polyelectrolyte used in the composition as defined above the neutral monomer is more particularly chosen from the N,N-dialkyl acrylamides, wherein each of the alkyl groups comprises between one and four carbon atoms and is in particular chosen from N,N-dimethyl acrylamide, N,N-diethyl acrylamide and N,N-dipropyl acrylamide.

In the definition of said cross-linked anionic polyelectrolyte used in the composition such as defined above, linear or branched alkyl radical comprising from eight to twenty carbon atoms means more particularly in formula (B) for R:
either a radical derived from linear primary alcohols such as for example, the octyl, decyl, undecyl, dodecyl, tridecyl, tetradecyl, pentadecyl, hexadecyl, heptadecyl, octadecyl, nonadecyl or eicosyl radical;
a radical derived from Guerbet alcohols, which are branched 1-alkanols complying with the general formula:

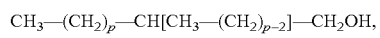

wherein p represents an integer number between 2 and 9, such as, for example, the 2-ethyl hexyl, 2-propyl heptyl, 2-butyl octyl, 2-pentyl nonyl, 2-hexyl decyl or 2-octyl dodecyl radicals; or
a radical derived from the isoalkanol complying with the general formula;

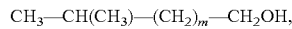

wherein m represents an integer number between 2 and 16, such as, for example, the 4-methyl pentyl, 5-methyl hexyl, 6-methyl heptyl, 15-methyl pentadecyl or 16-methyl heptadecyl radicals, or the 2-hexyl octyl, 2-octyl decyl or 2-hexyl dodecyl radicals.

According a particular aspect, the subject matter of the invention is a composition as defined above, characterised in that said cross-linked anionic polyelectrolyte comprises, for 100% molar of its constituent monomers:
from 20% molar to 80% molar of monomeric units issuing from the monomer comprising a partially or completely salified strong acid function;
from 15% molar to 75% molar of monomeric units issuing from a neutral monomer chosen from the N,N-dialkyl acrylamides, wherein each of the alkyl groups comprises between one and four carbon atoms;
from 0.5% molar to 5% molar of monomeric units issuing from a monomer of formula (B) as defined above.

According to another particular aspect, the subject matter of the invention is a composition such as defined above, characterised in that, in the definition of said crosslinked anionic polyelectrolyte, said neutral monomer is N,N-dimethyl acrylamide.

According to a particular aspect of this invention, the subject matter of the invention is a composition such as defined previously, characterised in that, in the definition of said crosslinked anionic polyelectrolyte, in formula (B) R designates more particularly an alkyl radical comprising 12 to 18 carbon atoms.

According to another particular aspect, the subject matter of the invention is a composition such as defined above, characterised in that, in the definition of said cross-linked anionic polyelectrolyte, in formula (B) n designates more particularly an integer number between 3 and 20.

According to an even more particular aspect the subject matter of the invention is a composition such as defined above, characterised in that, in the definition of said cross-linked anionic polyelectrolyte, said monomer of formula (B) is tetraethoxylated lauryl methacrylate.

According to an even more particular aspect the subject matter of the invention is a composition such as defined above, characterised in that, in the definition of said cross-linked anionic polyelectrolyte, said monomer of formula (B) is eicosaethoxylated stearyl methacrylate.

According to another particular aspect, the subject matter of the invention is a composition such as defined above, wherein said cross-linked anionic polyelectrolyte is cross-linked with a diethylenic or polyethylenic compound in the molar proportion expressed in relation to the monomers used, from 0.005% to 1%, more particularly from 0.01% to 0.5% and quite particularly from 0.01% to 0.25%. The cross-linking agent is more particularly chosen from ethylene glycol dimethacrylate, tetraallyloxyethane, ethylene glycol diacrylate, diallyl urea, triallyl amine, trimethylol propanetriacrylate or methylene-bis(acrylamide) or a mixture of these compounds.

The cross-linked anionic polyelectrolyte used in the composition as defined previously may also comprise various additives, such as complexing agents, transfer agents or chain-limiting agents.

According to a particular aspect, the subject matter of the invention is a composition as described above wherein said cross-linked anionic polyelectrolyte is chosen from the terpolymers of 2-methyl 2-[(1-oxo 2-propenyl)amino] 1-propane sulfonic acid partially salified in the form of ammonium, N,N-dimethyl acrylamide and tetraethoxylated lauryl methacrylate cross-linked with trimethylol propanetriacrylate, or the terpolymers of 2-methyl 2-[(1-oxo 2-propenyl)amino] 1-propanesulfonic acid partially salified in the form of ammonium salt, N,N-dimethyl acrylamide and eicosaethoxylated stearyl methacrylate, cross-linked with trimethylol propanetriacrylate.

According to an even more particular aspect, the subject matter of the invention is a composition as described above wherein said crosslinked anionic polyelectrolyte is a terpolymer of 2-methyl 2-[(1-oxo 2-propenyl)amino] 1-propanesulfonic acid partially salified in the form of ammonium, N,N-dimethyl acrylamide and tetraethoxylated lauryl methacrylate, cross-linked with trimethylol propanetriacrylate.

According to an even more particular aspect, the subject matter of the invention is a composition as described above wherein said crosslinked anionic polyelectrolyte comprises, for 100% molar:
from 60% molar to 80% molar of monomeric units issuing from 2-methyl 2-[(1-oxo 2-propenyl)amino] 1-propanesulfonic acid partially salified in the form of ammonium;
from 15% molar to 39.5% molar of monomeric units issuing from N,N-dimethyl acrylamide; and
from 0.5% molar to 5% molar of monomeric units issuing from tetraethoxylated lauryl methacrylate.

In the composition according to the invention, the in situ combination of the cross-linked anionic polyelectrolyte, polysorbate, polysaccharide gum and water, as defined above, constitutes the non-stringy system of said composition.

The aqueous phase included in the composition that is the subject matter of this invention contains water and may conventionally contain one or a plurality of cosmetically acceptable organic solvents. The cosmetically acceptable solvents may more particularly be chosen from the polyhydric alcohols such as for example glycerol, diglycerol, triglycerol, glycerol oligomers, xylitol, erythritol, sorbitol, 2-methyl-1,3-propanediol; alkoxylated polyhydric alcohols; glycols, such as for example butylene glycol, hexylene glycol, caprylyl glycol or 1,2 octanediol, pentylene glycol or 1,2 pentanediol, monopropylene glycol, dipropylene glycol, isoprene glycol, butyldiglycol, polyethylene glycols with a molecular weight of between 200 gmol$^{-1}$ and 8000 gmol$^{-1}$; or water-soluble alcohols such as for example ethanol, isopropanol or butanol.

In the composition, as defined above, salt means a heteropolar compound the crystalline lattice of which comprises the participation of at least one type of cation different to the hydrogen ions and at least one type of anion different to the hydroxide ions.

According to a particular aspect, the salt presented in dissolved form in the aqueous phase of the composition that is the subject matter of this invention is an inorganic salt or an organic salt.

Where the salt is inorganic, it may consist of a cation that is the ammonium ion or a metal cation and an anion selected from the elements of the group consisting of the halide ions, the carbonate ions, the bicarbonate ions, the phosphate anions, the nitrate anions, the borate anions and the sulphate anions. The salt may comprise a monovalent or multivalent metal cation chosen from the elements of the group consisting of the sodium, potassium, lithium, calcium, magnesium, zinc, manganese, iron, copper, cobalt, silver, gold, aluminium, barium, bismuth, selenium, zirconium, strontium and tin cations. The salt may be chosen from the group consisting of sodium chloride, calcium chloride, magnesium chloride, calcium sulphate, ammonium sulphate, calcium carbonate, zinc sulphate, magnesium sulphate, and sodium borate.

Where the salt is organic, it may consist of a cation that is an ammonium ion or a metal cation and an organic ion that is an organic compound having at least one carboxylic acid function in carboxylate form or at least one sulfonic acid function in sulfonate form or at least one sulphate function. The salt may consist of a monovalent or multivalent metal cation, more particularly chosen from the elements of the group consisting of the sodium, potassium, lithium, calcium, magnesium, zinc, manganese, iron, copper, cobalt, silver, gold, aluminium, barium, bismuth, selenium, zirconium, strontium and tin cations. The salt may consist of the cation chosen from the elements of the group consisting of the sodium, calcium, magnesium, zinc and manganese cations, and even more particularly the salt (S) is an organic salt consisting of the sodium cation. The salt may consist of a cation that is the ammonium ion or a metal cation as described above, and an organic ion that is an organic compound having at least one carboxylic acid function in carboxylate form chosen from the elements of the group consisting of glycolic acid, citric acid, tartaric acid, salicylic acid, lactic acid, mandelic acid, ascorbic acid, pyruvic acid, fumaric acid, retinoic acid, benzoic acid, kojic acid, malic acid, gluconic acid, galacturonic acid, propionic acid, heptanoic acid, 4-amino benzoic acid, cinnamic acid, benzalmalonic acid, aspartic acid and glutamic acid. The salt may be selected from the elements in the group consisting of sodium glycolate, sodium citrate, sodium salicylate, sodium lactate, sodium gluconate, zinc gluconate, manganese gluconate, copper gluconate and magnesium aspartate. The salt may consist of a cation that is the ammonium ion or a metal cation as described above, and an organic anion that is an organic compound having at least one sulfonic acid function in sulfonate form chosen from the elements of the group consisting of 2-phenylbenzimidazole-5-sulfonic acid, the sulfonic acids derived from benzophenones, such as for example 4-hydroxy-2-methoxy 5-(oxo-phenylmethyl)benzenesulfonic acid (said acid being registered under the name Benzophenone-4), the sulfonic acids derived from 3-benzylidene camphor such as for example 4-(2-oxo-3-bornylidenemethyl)benzene sulfonic acid, 2-methyl 5-(2-oxo-3-bornylidenemethyl)benzene sulfonic acid. The salt may be selected from the group consisting of sodium 2-phenylbenzimidazole-5 sulfonate and sodium 4-hydroxy 2-methoxy 5-(oxo-phenylmethyl)benzene sulfonate. 2-phenyl benzimidazole-5-sulfonic acid is marketed in particular under the brand name EUSOLEX™ 232 by the company Merck. Sodium 4-hydroxy-2-methoxy-5-(oxo-phenylmethyl)benzene sulfonate is registered under the name Benzophenone-5.

In general terms, the composition that is the subject matter of this invention comprises, in addition to the stabilising system as defined above, adjuvants and/or additives routinely used in the field of cosmetic formulations.

Among the adjuvants likely to be present in the compositions that are the subject matter of this invention, the following can be cited: exfoliating agents, anti-inflammatory agents, skin soothers, film-forming compounds, hydrotropic agents, plasticizing agents, opacifying agents, pearlescent agents, superfatting agents, sequestering agents, chelating agents, non-ionic detergent surfactants, antioxidant agent, perfumes, preservatives, conditioning agents, active ingredients intended to provide a treating action on the skin, mineral fillers or pigments, particles procuring a visual effect or intended for encapsulating active ingredients, exfoliating particles, texture agents, optical brighteners, insect repellents.

The low-pH compositions of the present invention can be effective as compositions that exfoliate the skin. Exfoliation aids the removal of dead skin cells from the skin. Mild acids are known to be effective at exfoliating the skin and therefore, in one embodiment, the compositions of the present invention comprise one or more mild acids.

In one embodiment, the one or more mild acids are selected from alpha-hydroxy acid (AHAs) and/or beta-hydroxy acids (BHAs), more preferably alpha-hydroxy acids. AHAs and BHAs have the general chemical formula of HO-$(CR_1R_2)_n$—COOH, where n is 1 with respect to AHAs and n is 2 with respect to BHAs. With respect to BHAs, $R_1$ and/or $R_2$ may differ when comparing the α-carbon substituents against the β-carbon substituents.

In one embodiment, the mild acids are selected from the list consisting of glycolic acid, lactic acid, citric acid, malic acid, tartaric acid, gluconic acid (and/or gluconolactone, which partially hydrolyses to gluconic acid in solution), mandelic acid, ascorbic acid, phytic acid, salicylic acid, aleuritic acid, hydroxytetronic acid, glucuronic acid, hyaluronic acid, mucic acid, galacturonic acid, saccharic acid, glucoheptonic acid, α-hydroxybutyric acid, tartronic acid, α-hydroxyisobutyric acid, isocitric acid, α-hydroxyisocaproic acid, dihydroxymaleic acid, α-hydroxyisovaleric acid, dihydroxy-tartaric acid, β-hydroxybutyric acid, dihydroxyfumaric acid, β-phenyllactic acid, atrolactic acid, galactonic acid, pantoic acid, glyceric acid and combinations thereof. In one embodiment the mild acid is glycolic acid. Combination of mild acids are particular importance include (1) the combination of glycolic acid with gluconolactone, (2) the combination of glycolic acid with lactic acid, citric acid, malic acid and tartaric acid and (3) the combination of glycolic acid with lactic acid, citric acid, malic acid, tartaric acid and gluconolactone.

In one embodiment, the one or more mild acids are present within the composition at a concentration of between 1 wt. % and 20 wt. %, preferably between 2 wt. % and 15 wt. %, more preferably between 4 wt. % and 10 wt. %.

In one embodiment, the composition comprises at least one anti-inflammatory agent. The term "anti-inflammatory agent" is intended to mean an agent which provides an anti-inflammatory benefit as would be understood by a person skilled in the art.

The anti-inflammatory agent may be selected from the group consisting of a glycyrrhizic acid or glycyrrhizic acid derivative (such as monoammonium glycyrrhizate (MAG)), panthenol, α-bisabolol, betaine, lipochroman, tocopheryl acetate, phytosphingosine, extracts of green tea, extracts of *Sophora flavescens* root extract, extracts of chamomile (e.g. *Anthemis nobilis*), extracts of Aloe vera, extracts of Echinacea, extracts of willow bark, extracts of willow herb, extracts of almond, extracts of oats, extracts of Kola, extracts of red clover, salicylic acid, xymeninic acid, turmeric, and combinations thereof.

The anti-inflammatory agent may be selected from the group consisting of a glycyrrhizic acid or glycyrrhizic acid derivative (such as MAG), panthenol, α-bisabolol, betaine, lipochroman, tocopheryl acetate, phytosphingosine, extracts of green tea, and combinations thereof. Preferably the anti-inflammatory agent is a glycyrrhizic acid or glycyrrhizic acid derivative, more preferably MAG.

The anti-inflammatory agent may be present in an amount that produces an inhibitory effect on interleukin-6 (IL-6). For example, the anti-inflammatory agent may produce more than about 40% interleukin-6 inhibition, more than about 50% interleukin-6 inhibition, more than about 60% interleukin-6 inhibition, more than about 70% interleukin-6 inhibition, more than about 75% interleukin-6 inhibition, more than about 80% interleukin-6 inhibition, more than about 90% interleukin-6 inhibition, more than about 99% interleukin-6 inhibition, or 100% interleukin-6 inhibition. In one embodiment, the anti-inflammatory agent, at a concentration of 0.01% by weight of the cosmetic composition, produces more than about 40% interleukin-6 inhibition, more than about 50% interleukin-6 inhibition, more than about 60% interleukin-6 inhibition, more than about 70% interleukin-6 inhibition, more than about 75% interleukin-6 inhibition, more than about 80% interleukin-6 inhibition, more than about 90% interleukin-6 inhibition, more than about 99% interleukin-6 inhibition, or 100% interleukin-6 inhibition. A suitable technique for measuring IL-6 inhibition is described in detail later on in the specification.

The anti-inflammatory agent may be present in an amount of about 0.001% to about 20% by weight of the composition, about 0.01% to about 15% by weight of the composition, about 0.1% to about 10% by weight of the composition, about 1% to about 5% by weight of the composition, about 1% to about 3% by weight of the composition. In one embodiment, the anti-inflammatory agent is present in an amount of about 1.5% to about 3% by weight of the composition.

Among the opacifying and/or pearlescent agents that can be associated with the composition that is the subject matter of this invention, the following can in particular be cited: sodium or magnesium palmitates, stearates or hydroxylstearates, ethylene or polyethylene glycol monostearates or distearates, fatty alcohols, styrene homopolymers and copolymers such as the styrene acrylate copolymer marketed under the name MONTOPOL™ OP1 by the company SEPPIC.

Among the texture agents that can be associated with the composition that is the subject matter of this invention, mention may be made of: N-acyl derivatives of amino acids, such as for example the lauroyl lysine marketed under the name AMINOHOPE™ LL by the company AJINOMOTO, the octenyl starch succinate marketed under the name DRY-FLO™ by the company NATIONAL STARCH, the myristyl polyglucoside marketed by SEPPIC under the name MONTANOV™ 14, cellulose fibres, cotton fibres, chitosan fibres, talc, sericite, mica.

Among the active ingredients that can be associated with the composition that is the subject matter of this invention, mention may be made for example of: vitamins and derivatives thereof, in particular the esters thereof, such as retinol (vitamin A) and the esters thereof (retinyl palmitate for example), ascorbic acid (vitamin C) and the esters thereof, ascorbic acid sugar derivatives (such as for example ascorbyl glucoside), tocopherol (vitamin E) and the esters thereof (such as for example tocopherol acetate), vitamin B3 or B10 (niacinamide and derivatives thereof); the compounds showing a skin lightening or depigmenting action, such as for example SEPIWHITE™ MSH, arbutin, kojic acid, hydroquinone, VEGEWHITE™, GATULINE™, SYNERLIGHT™, BIOWHITE™, MELASLOW™, PHYTOLIGHT™, DERMALIGHT™, CLARISKIN™, DERMAWHITE™, ETHIOLINE™, MELAREST™, GIGAWHITE™, ALBATINE™, LUMISKIN™; the compounds showing a calming action such as SEPICALM™ S, allantoin and bisabolol; anti-inflammatory agents, compounds showing a moisturising action such as for example urea, hydroxyureas, glycerol, polyglycerols, AQUAXYL™, glycerolglucoside; polyphenols extracts such as for example grape extracts, pine extracts, wine extracts, olive extracts; compounds showing a slimming or lipolytic action such as caffeine or derivatives thereof, ADIPOSLIM™, ADIPOLESS™; N-acylated proteins; N-acylated peptides such as for example MATRIXIL™; N-acylated amino acids; partial hydrolysates of N-acylated proteins; amino acids; peptides; total protein hydrolysates, soya bean extracts, for example Raffermine™; wheat extracts, for example TENSINE™ or GLIADINE™; plant extracts, such as plant extracts enriched in tannins, plant extracts enriched in isoflavones or plant extracts enriched in terpenes; fresh or sea water alga extracts; marine extracts in general such as corals; essential waxes; bacterial extracts; ceramides; phospholipids; compounds showing an antimicrobial action or a purifying action, such as for example LIPACIDE™ CBG, LIPACIDE™ UG, SEPICONTROL™ A5; OCTOPIROX™ or SENSIVA™ SC50; the compounds showing an energising or tonic property such as Physiogenyl™, panthenol and derivatives thereof such as SEPICAP™ MP; anti-aging agents such as SEPILIFT™ DPHP, SEPIVINOL™, SEPIVITAL™, MANOLIVA™, PHYTO-AGE™, TIMECODE™; SURVICODE™, LIPACIDE™ PVB; anti-photoaging agents; agents protecting the integrity of the dermo-epidermic junction; agents increasing the synthesis of components of the extracellular matrix such as for example collagen, elastins, glycosaminoglycans; agents promoting chemical cell communication such a cytokines or physical cell communication such as integrins; agents creating a "warming" sensation on the skin such as skin microcirculation activators (such as for example nicotinic acid derivatives); or products creating a "cooling" sensation on the skin (such as for example menthol and derivatives); agents improving skin microcirculation, for example veinotonics; draining agents; agents for decongestant purposes such as for example extracts of gingko biloba, ivy, horse chestnut, bamboo, ruscus, butcher's broom, *Centalla asiatica*, fucus, rosemary and willow.

Among the active ingredients that can be associated with the composition that is the subject matter of this invention, the following can more particularly be cited: skin tanning or browning agents, such as for example dihydroxyacetone, isatin, alloxan, ninhydrin, glyceraldehyde, mesotartric aldehyde, glutaraldehyde, erythrulose.

Among the non-ionic detergent surfactants that can be associated with the compound that is the subject matter of this invention, mention may be made of fatty alcohol ethoxylated derivatives comprising 8 to 12 carbon atoms, fatty acid ethoxylated derivatives comprising 8 to 12 carbon atoms, fatty ester ethoxylated derivatives comprising 8 to 12 carbon atoms, monoglyceride ethyoxylated derivatives comprising 8 to 12 carbon atoms, alkylpolyglucosides of formula (II):

$$R_2\text{—}O\text{—}(S)_y\text{—}H \quad (II)$$

wherein y represents an integer between 1 and 5, S represents the a reducing sugar residue and $R_2$ represents a saturated or unsaturated, linear or branched alkyl radical, having 5 to 16 carbon atoms, preferably 8 to 14 carbon atoms, or a mixture of compounds of formula (II).

The non-ionic detergent surfactants that can be associated with the composition that is the subject matter of this invention are more particularly chosen from the elements of the group consisting of caprylyl capryl glucosides, marketed in particular under the brand name ORAMIX™ CG 110 by the company SEPPIC, decylglucoside, marketed in particular under the brand name ORAMIX™ NS 10 by the company SEPPIC.

Among the pigments that can be associated with the composition that is the subject matter of this invention, mention may be made of titanium dioxide: titanium dioxide, brown iron oxides, yellow iron oxides, black iron oxides or red iron oxides, or white or coloured pearlescent pigments such as Mica-Titanium.

According to another particular aspect, the subject matter of the invention is a composition as defined above, characterised in that the viscosity thereof, measured at a temperature of 23° C., is between 15,000 centipoise (cP, equivalent to 15 Pascal seconds (Pa·s)) and 45,000 cP (45 Pa·s), preferably between 17,000 cP (17 Pa·s) and 40,000 cP (40 Pa·s), more preferably between 20,000 cP (20 Pa·s) and 30,000 cP (30 Pa·s). Viscosity is a measure of its resistance to gradual deformation by shear stress or tensile stress, where a liquid with a greater viscosity has a greater resistance to gradual deformation (and in an informal sense is "thicker") than a liquid with a lesser viscosity. The skilled person would be well aware of how to determine the viscosity of a given liquid.

A suitable method for measuring viscosity is presented in Example 3, in particular using a Brookfield RVDV-I Prime viscometer with a heliopath, a 120 ml capacity polypropylene plastic container with a diameter of 50 mm and a height of 72 mm, a speed of 10 revolutions per minute (rpm) for a time of 30 seconds using T Bar spindle 93. In all of the embodiments discussed above, viscosity is measured at 23° C.

The composition of the invention has a pH of between 2 and 6 (i.e. acidic pH). In one embodiment, the composition has a pH of between 3 and 5, more preferably between 3.6 and 4.1.

The composition that is the subject matter of this invention may be in the form of a microemulsion.

The composition that is the subject matter of this invention can be used by application to the skin, preferably of a direct application.

Product-By-Process

According to another aspect, the subject matter of this invention is a composition defined above obtainable by a process comprising the following steps:

(a) in one vessel, homogenising the polysaccharide gum (iii) into the aqueous phase comprising the water at a temperature of between 60° C. and 90° C.;
(b) in a vessel separate from that in (a), homogenising the cross-linked anionic polyelectrolyte (i) and the polysorbate (ii) into the oil phase at a temperature of between 60° C. and 90° C.; and
(c) combining the ingredients of (a) with the ingredients of (b) through homogenisation at a temperature of between 60° C. and 90° C.

In the method that is the subject matter of the invention, the oil phase comprises one or a plurality of oils as defined above.

In case the oil phase does not consist of a single oil or a single wax, the oil phase is prepared by mixing the constituent ingredients thereof at a temperature typically between 20° C. and 85° C., and even more particularly at a temperature between 20° C. and 60° C., and by means of any mixing device known to persons skilled in the art, such as for example by means of a mechanical stirring device equipped with an "anchor" type mobile assembly, at stirring speeds of between 50 revolutions/minute (rpm) and 500 rpm, more particularly between 50 rpm and 300 rpm.

In the process that is the subject matter of the invention as described above, any one or combination of steps (a), (b) and (c) (preferably all steps) may be performed by means of any mixing device known to the person skilled in the art, such as for example by means of a mechanical stirring device equipped with an "anchor" type mobile assembly, at stirring speeds of between 200 rpm and 500 rpm, more particularly between 250 rpm and 300 rpm, and such as for example by means of a stirring device of the rotor-stator type at stirring speeds of between 100 rpm and 10,000 rpm, more particularly between 500 rpm and 4,000 rpm.

In the process that is the subject matter of the invention, any one or combination of steps (a), (b) and (c) (preferably all steps) may be implemented at a temperature of between 65° C. and 85° C., more particularly at a temperature of between 68° C. and 80° C., and even more particularly at a temperature of between 70° C. and 75° C.

In the process that is the subject matter of the invention as described above, the cosmetically acceptable aqueous phase comprises water, and optionally one or a plurality of cosmetically acceptable organic solvents as described previously, and from 1% to 25% by weight for 100% of the weight of said cosmetically acceptable aqueous phase of at least one salt in presented in a dissolved form and as defined previously.

In one embodiment, the cosmetically acceptable aqueous phase is prepared by mixing water, and optionally one or a plurality of cosmetically acceptable organic solvents, with at least one salt as described previously, at a temperature of between 20° C. and 85° C., and even more particularly at a temperature of between 20° C. and 60° C., and by means of any mixing device known to persons skilled in the art, such as for example by means of a mechanical stirring device equipped with an anchor type mobile assembly, at stirring speeds of between 50 rpm and 500 rpm, more particularly 20 between 50 rpm and 300 rpm.

The composition obtainable by a process defined above is stable over time after a period of storage of at least one month at 20° C. and retains a homogeneous appearance, not showing the appearance of lumps of clusters, after of the same storage period under the same experimental conditions.

"Homogenisation" is understood in the art to mean any process used to make a mixture of two mutually non-soluble liquids the same throughout. This is achieved by turning one of the liquids into a state consisting of extremely small particles distributed uniformly throughout the other liquid, forming an emulsion. Typically homogenisation is carried out through rapid stirring. The speed necessary homogenise a two non-soluble liquids is dependent on a number of factors such as homogenisation time, the nature of the liquids being homogenised and the scale of manufacture. The skilled person would be well aware of how to optimise a homogenisation process in order to carry out the process of the present invention.

Use

According to another aspect, the subject matter of this invention is the cosmetic use of the composition as defined above for cleansing, protection and/or care of the skin. Within the scope of this invention, "cosmetic use" means uses of the composition intended to improve and/or preserve the external aesthetic appearance of the skin.

According to a more particular aspect, the composition that is the subject matter of this invention can be used as a peel mask. Accordingly, in one aspect, the present invention provides a method in caring for the skin comprising applying the composition defined above to the region of skin of interest, leaving the composition on the skin for between 2 and 20 minutes (preferably 5 to 15 minutes, more preferably between 8 and 12 minutes) and rinsing the composition from the skin. In one embodiment, "caring for the skin" includes one or more of removing dead skin cells, renewing skin complexion, improving the radiance of the skin, reducing the appearance of fine lines and wrinkles, reducing congestion, reducing blackheads, reducing comedones and/or reducing blemishes.

The following examples illustrate the invention without however limiting it.

EXAMPLES

Example 1

Manufacture of aterpolymer of ammonium 2-methyl 2-[(1-oxo 2-propenyl)amino] 1-propanesulfonate, N,N-dimethyl acrylamide and tetraethoxylated lauryl methacrylate [AMPS/DMAM/MAL(4OE) 77.4/19.2/3.4 molar], cross-linked with trimethylol propanetriacrylate (TMPTA) (polyelectrolyte A)

592 g of an aqueous solution containing 15% by weight of ammonium 2-methyl 2-[(1-oxo 2-propenyl)amino] 1-propanesulfonate in a tert-butanol/water mixture (97.5/2.5 by volume), 10.1 g of N,N dimethyl acrylamide, 4.2 g of tetraethoxylated lauryl methacrylate and 0.75 g of trimethylol propanetriacrylate are loaded into a reactor maintained at 25° C. under stirring.

After sufficient time to achieve satisfactory homogenisation of the solution, the solution is deoxygenated by bubbling nitrogen heated to 70° C., 0.42 g of dilauroyl peroxide is then added and the reaction medium is then maintained at 70° C. for approximately 1 hour and 80° C. for approximately 2 hours. After cooling, the powder that formed during polymerisation is filtered and dried to obtain the required product, hereinafter referred to as "polyelectrolyte A".

Example 2

Method of Manufacture of Paste Formulations

Method 1—In a main vessel polyelectrolyte A was combined with water through homogenisation at 3,500 rpm and at 70° C., forming the aqueous phase. Xanthan gum (Keltrol RD) was then added, followed by further homogenisation at 3,500 rpm and at 70° C. In a support vessel, polysorbate 60 was combined with an oil phase (comprising jojoba oil) at 70° C. through stirring. The contents of the support vessel was then added to a main vessel and homogenised at 3,500 rpm and at 70° C. The composition was then cooled to 30° C.

The resulting formulation comprised of lumps of xanthan gum and of polyelectrolyte A.

Method 2—In a main vessel polyelectrolyte A was combined with water through homogenisation at 3,500 rpm and at 75° C., forming a portion of the aqueous phase. Xanthan gum (Keltrol RD) was premixed with a further portion of aqueous phase, followed by homogenisation at 3,500 rpm and at 75° C. In a support vessel, polysorbate 60 was combined with an oil phase (comprising jojoba oil) at 70° C. through stirring. The contents of the support vessel was then added to a main vessel and homogenised at 3,500 rpm and at 70° C. The composition was then cooled to 30° C.

The resulting formulation comprised of lumps of xanthan gum and of polyelectrolyte A before cooling took place.

Method 3—In a support vessel, polysorbate 60 was combined with an oil phase (comprising jojoba oil) at 75° C. through stirring. Polyelectrolyte A was then added, followed by homogenisation at 3,500 rpm and at 75° C. The content of the support vessel was then added to a main vessel comprising water, followed by homogenisation at 3,500 rpm and at 75° C. for five minutes. Xanthan gum (Keltrol RD) was then added, followed by further homogenisation at 3,500 rpm and at 75° C. for five minutes. The composition was then cooled to 30° C.

The resulting formulation comprised lumps of xanthan gum.

Method 4—In a main vessel, xanthan gum (Keltrol RD) was homogenised with water at 3,500 rpm and at 70° C. In a support vessel, polysorbate 60 was combined with an oil phase (comprising jojoba oil) at 75° C. through stirring. Polyelectrolyte A was then added, followed by homogenisation at 3,500 rpm and at 75° C. The content of the support vessel was then added to a main vessel, followed by homogenisation at 3,500 rpm and at 75° C. for five minutes. The composition was then cooled to 30° C.

The resulting formulation comprised no lumps.

Summary—Various methods of manufacture were carried out but the only method that was effective in combining the polyelectrolyte A, polysorbate, polysaccharide gum, oil and water without forming lumps was method 4, i.e. homogenising the polysaccharide gum with water, then separately homogenising the polyelectrolyte A, polysorbate and oil, then homogenising the aqueous phase with the oil phase. All of the formulations discussed in Example 3 were manufactured according to Method 4.

Example 3

Assessment of Formulation Variations

Paste formulations with varying levels polyelectrolyte A, polysorbate 60, xanthan gum and water were manufactured according to Method 4. The concentration of jojoba oil present in the formulations was kept constant at 5 wt. %. These formulations all had a pH of between 3.8 and 4.0. Tables 1 and 2 provide details regarding the concentration variations (as a weight percentage), the viscosity (measured at 23° C.) and appearance of each formulation. All formulations below comprise exfoliants in the form of (a) 14 wt.

% "ACB Fruit Mix" from Active Concepts (300/O), or (b) 7 wt. % glycolic acid and 3 wt. % gluconolactone (300/Z, 300/AB and 300/AD), or (c) 7 wt. % glycolic acid, 3 wt. % gluconolactone and 1 wt. % "ACB Fruit Mix" (300/AG, 300/AE, 300/AF and 300/AL). "ACB Fruit Mix" in itself comprises 28.5 wt. % *Vaccinium myrtillus* fruit/leaf extract, 12 wt. % *Saccharum officinarum* (Sugarcane) extract, 4 wt. % *Citrus limon* fruit extract, 4 wt. % *Citrus aurantium dulcis* (Orange) fruit extract and 1.5 wt. % *Acer saccharum* (Sugar maple) extract, these extracts providing between 14 wt. % and 16 wt. % lactic acid, between 6 wt. % and 8.5 wt. % glycolic acid, between 1 wt. % and 3 wt. % citric acid, less than 0.5 wt. % malic acid and less than 0.5 wt. % of tartaric acid.

Viscosity as described in the present invention is measured using a Brookfield RVDV-I Prime E viscometer plus Model D220 helipath stand and motor, equipped with RV T-bar spindle 93 (C). Viscosity measurements were obtained as follows: (1) Ensure the sample product has a temperature of 23° C. and that it is not aerated. Sample is presented in a 120 ml capacity polypropylene plastic container with a diameter of 50 mm and a height of 72 mm; (2) Before measurement, auto-zero the viscometer after switching on the unit by following the on-screen instructions with no spindle attached to the viscometer; (3) Select the T-bar spindle 93 (C); (4) Select the revolution speed "10". This will rotate the spindle at 10 rpm; (5) Carefully attach the spindle to the lower shaft of the viscometer; (6) Lower the spindle into the sample product until the spindle is 5 mm away from the base of the container. Ensure that the spindle is not in contact with the sides or base of the sample; (7) Press the "Timed Option" buttons; (8) Use the Up and Down arrows to select the "Timed Stop" option then press "Enter" to confirm; (9) Use the Up and Down arrows to select zero minutes, then press "Enter" to confirm (10) Use the Up and Down arrows to select 30 seconds, then press "Enter" to confirm; (11) Switch on the helipath stand motor; (12) Press the "Motor On/Off" button to begin the measurement; (13) The viscometer will display a countdown from 30 seconds, after which it will display the final viscosity measured; and (14) Record the viscosity reading.

TABLE 1

| Formulation | 300/O | 300/Z | 300/AB | 300/AG | 300/AD |
|---|---|---|---|---|---|
| Polyelectrolyte A | 1.9% | 0.95% | 0.95% | 1.48% | 1.9% |
| Polysorbate 60 | 10% | 10% | 10% | 10% | 6% |
| Xanthan Gum | 0.25% | 1% | 0.5% | 0.5% | 0.25% |
| Water | 21.99% | 18.63% | 17.71% | 17.41% | 20.67% |
| Viscosity (cP) | 29000 | 51900 | 35000 | 30800 | 25900 |
| Appearance | Translucent and non-stringy | Stringy | Stringy | Stringy | Translucent and non-stringy |

TABLE 2

| Formulation | 300/AE | 300/AL | 300/AF | 300/AH | 300/AI |
|---|---|---|---|---|---|
| Polyelectrolyte A | 1.9% | 1.9% | 1.9% | 1.9% | 1.9% |
| Polysorbate 60 | 0% | 6% | 6% | 0% | 0% |
| Polysorbate 20 | 0% | 0% | 0% | 6% | 0% |
| Polysorbate 80 | 0% | 0% | 0% | 0% | 6% |
| Xanthan Gum | 0.25% | 0.25% | 0.25% | 0.25% | 0.25% |
| Water | 23.18% | 60.69% | 20.37% | 20.37% | 20.37% |
| Viscosity (cP) | 36100 | <10000 | 38000 | 21900 | 30000 |
| Appearance | Opaque | Opaque | Translucent and non-stringy | Translucent and non-stringy | Translucent and non-stringy |

Summary—Tables 1 and 2 show that, in order to achieve a non-stringy, translucent formulation, polysorbate and xanthan gum are necessary. Polyelectrolyte A is necessary at a concentration greater than 1.48%, and a water concentration of less than 60.69% is also necessary. Polysorbate 60, polysorbate 20 and polysorbate 80 are all equally effective at producing a translucent, non-stripy composition.

Example 4

Clinical Assessment of 300/AF

300/AF (a paste formulation comprising glycerin, water, glycolic acid, polysorbate 60, jojoba seed oil, gluconolactone, ammonium glycyrrhizate, polyacrylate A, potassium hydroxide, panthenol, "Multifruit BSC colour improved", xanthan gum, bisabolol, sodium PCA, T-butyl alcohol, magnesium PCA, tetrasodium EDTA, zinc PCA, manganese PCA, phenoxyethanol and potassium sorbate) was tested by 35 volunteers. Volunteers were all women aged between 30 and 50, with a mix of skin types and ethnicities. All volunteers self-diagnosed as having at least one of uneven skin tone, texture, dull complexion, visible pores and age spots. Volunteers were asked to apply 300/AF to the face, leave on for ten minutes, remove with a cloth, and repeat this process two to three times a week (not on consecutive days) for four weeks.

Volunteers found 300/AF easy to use (100%), enjoyed the process of using the product (95.6%), found that this product was gentle on their skin after four weeks (97.1%), rated the product after four weeks (100%) and stated that they would likely buy the product (100%). Comments during the study included that the product felt pleasant on the skin.

The invention claimed is:

1. A composition in the form of an oil-in-water emulsion having a viscosity of between 15 Pa·s and 45 Pa·s at 23° C., having a pH of between 2 and 6 and comprising
   (i) at least 1.6 wt. % of at least one cross-linked anionic polyelectrolyte resulting from the polymerisation of partially or completely salified 2-methyl 2-[(1-oxo 2-propenyl)amino] 1-propane sulfonic acid, with at least one neutral monomer chosen from N,N-dialkyl acrylamides, wherein each of the alkyl groups comprises between one and four carbon atoms, and at least one monomer of formula (B):

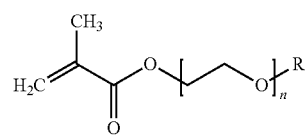

(B)

wherein R represents a linear or branched alkyl radical comprising eight to twenty carbon atoms and n represents a number greater than or equal to one and less than or equal to twenty, in the presence of at least one cross-linking agent;
   (ii) at least 4 wt. % of at least one polysorbate;
   (iii) at least 0.1 wt. % of at least one polysaccharide gum; and
   (iv) between 6 wt. % and 30 wt. % water.

2. The composition of claim 1, wherein the composition has a pH of between 3 and 5.

3. The composition of claim 1, wherein the fatty acid associated with the polyoxyethylene sorbitan part of the polysorbate comprises between sixteen and eighteen carbon atoms.

4. The composition of claim 1, wherein the at least one polysorbate is present at a concentration of between 4 wt. % and 20 wt. %.

5. The composition of claim 1, wherein the polysaccharide gum is uncharged.

6. The composition of claim 1, wherein the at least one polysaccharide gum is present at a concentration of between 0.01 wt. % and 1 wt. %.

7. The composition of claim 1, wherein water is present at a concentration of between 10 wt. % and 28 wt. %.

8. The composition of claim 1, wherein the neutral monomer of the at least one cross-linked anionic polyelectrolyte is N,N-dimethyl acrylamide, acrylamide or (2-hydroxy-ethyl) acrylate.

9. The composition of claim 1, wherein in formula (B), R represents an alkyl radical having between 12 and 18 carbon atoms.

10. The composition of claim 1, wherein the at least one polyelectrolyte is present at a concentration of between 1.6 wt. % and 4 wt. %.

11. The composition of claim 1, wherein the composition has a viscosity of between 17 Pa·s and 45 Pa·s.

12. The composition of claim 1, wherein the composition further comprises a mild acid suitable for exfoliating the skin.

13. The composition of claim 12, wherein the mild acid is selected from the list comprising glycolic acid, lactic acid, citric acid, malic acid, tartaric acid and combinations thereof.

14. The composition of claim 1 obtainable by a process comprising the following steps:
(a) in one vessel, homogenising the polysaccharide gum (iii) into the aqueous phase comprising the water at a temperature of between 60° C. and 90° C.;
(b) in a vessel separate from that in (a), homogenising the cross-linked anionic polyelectrolyte (i) and the polysorbate (ii) into the oil phase at a temperature of between 60° C. and 90° C.; and
(c) combining the ingredients of (a) with the ingredients of (b) through homogenisation at a temperature of between 60° C. and 90° C.

15. The composition of claim 1, wherein the composition has a pH of between 3.4 and 4.5.

16. The composition of claim 3, wherein the fatty acid is saturated.

17. The composition of claim 1, wherein the at least one polysorbate is present at a concentration of between 6 wt. % and 10 wt. %.

18. The composition of claim 1, wherein the polysaccharide gum is xanthan gum.

19. The composition of claim 1, wherein the at least one polysaccharide gum is present at a concentration of between 0.1 wt. % and 0.5 wt. %.

* * * * *